(12) United States Patent
Salini

(10) Patent No.: US 9,216,157 B2
(45) Date of Patent: Dec. 22, 2015

(54) CHEWING GUM IN THE FORM OF MULTI-LAYER TABLETS

(75) Inventor: Alberto Salini, Lugano (CH)

(73) Assignee: Jagotec AG, Muttenz (CH)

( * ) Notice: Subject to any disclaimer, the term of this patent is extended or adjusted under 35 U.S.C. 154(b) by 2123 days.

(21) Appl. No.: 10/545,348

(22) PCT Filed: Jan. 20, 2004

(86) PCT No.: PCT/EP2004/000371
§ 371 (c)(1),
(2), (4) Date: Mar. 31, 2006

(87) PCT Pub. No.: WO2004/073691
PCT Pub. Date: Sep. 2, 2004

(65) Prior Publication Data
US 2006/0204451 A1 Sep. 14, 2006

(30) Foreign Application Priority Data
Feb. 20, 2003 (EP) .................................... 03003813

(51) Int. Cl.
| | | |
|---|---|---|
| A23G 4/00 | (2006.01) | |
| A23G 4/18 | (2006.01) | |
| A23L 1/236 | (2006.01) | |
| A61K 9/20 | (2006.01) | |
| A23G 3/34 | (2006.01) | |
| A23G 4/04 | (2006.01) | |
| A23G 4/12 | (2006.01) | |
| A23G 4/20 | (2006.01) | |
| A61K 9/68 | (2006.01) | |

(52) U.S. Cl.
CPC .............. *A61K 9/2086* (2013.01); *A23G 3/008* (2013.01); *A23G 4/04* (2013.01); *A23G 4/046* (2013.01); *A23G 4/126* (2013.01); *A23G 4/20* (2013.01); *A61K 9/0058* (2013.01)

(58) Field of Classification Search
USPC ...................... 426/3, 548, 549, 660; 424/464
See application file for complete search history.

(56) References Cited

U.S. PATENT DOCUMENTS

| | | | |
|---|---|---|---|
| 4,139,589 A | 2/1979 | Beringer et al. ............... 264/250 |
| 4,648,316 A | 3/1987 | Ruffinatti | |
| 4,753,805 A | 6/1988 | Cherukuri et al. ................. 426/5 |
| 4,999,058 A * | 3/1991 | Kawashima et al. .......... 536/4.1 |
| 5,017,385 A | 5/1991 | Wienecke | |
| 5,286,500 A | 2/1994 | Synosky et al. | |
| 5,409,715 A | 4/1995 | Meyers | |
| 5,626,874 A * | 5/1997 | Conte et al. .................... 424/464 |
| 6,294,200 B1 * | 9/2001 | Conte et al. .................... 424/472 |
| 6,303,159 B2 * | 10/2001 | Barkalow et al. ................. 426/5 |
| 2001/0002998 A1 | 6/2001 | Ream et al. | |
| 2001/0021830 A1 | 9/2001 | Yamada et al. | |
| 2002/0122843 A1 * | 9/2002 | McGrew et al. .................. 426/3 |
| 2005/0008747 A1 * | 1/2005 | Barkalow et al. ............. 426/548 |
| 2005/0031677 A1 * | 2/2005 | Pather et al. .................... 424/448 |
| 2006/0147580 A1 * | 7/2006 | Nissen et al. ...................... 426/3 |

FOREIGN PATENT DOCUMENTS

| | | |
|---|---|---|
| EP | 0151344 A2 | 8/1985 |
| EP | 1594478 | 12/2007 |
| JP | 4252143 A | 9/1992 |

OTHER PUBLICATIONS

Notice of Opposition against EP 1 594 478 B1 dated Sep. 4, 2008.
Response to Notice of Opposition against EP1 594 478 B1 dated May 26, 2009.

* cited by examiner

*Primary Examiner* — Michele L Jacobson
*Assistant Examiner* — Bhaskar Mukhopadhyay
(74) *Attorney, Agent, or Firm* — Mintz Levin Cohn Ferris Glovsky and Popeo, P.C.; Muriel Liberto, Esq.

(57) ABSTRACT

Disclosed are tablets having a sandwich-like structure comprising at least one inner layer of gum base containing one or more active pharmaceutical, dietetic or nutritional ingredients and two non-contigous outer layers comprising antiadhesion excipients and compression adjuvants preventing the adhesion to the punches of the tabletting machine and possibly active ingredients which are the same as or different from those present in the inner layer. Said tablets are obtainable by direct compression of mixtures or granulates of the various components of each layer.

11 Claims, 2 Drawing Sheets

CHEWING GUM IN THE FORM OF MULTI-LAYER TABLETS

Figure 1:
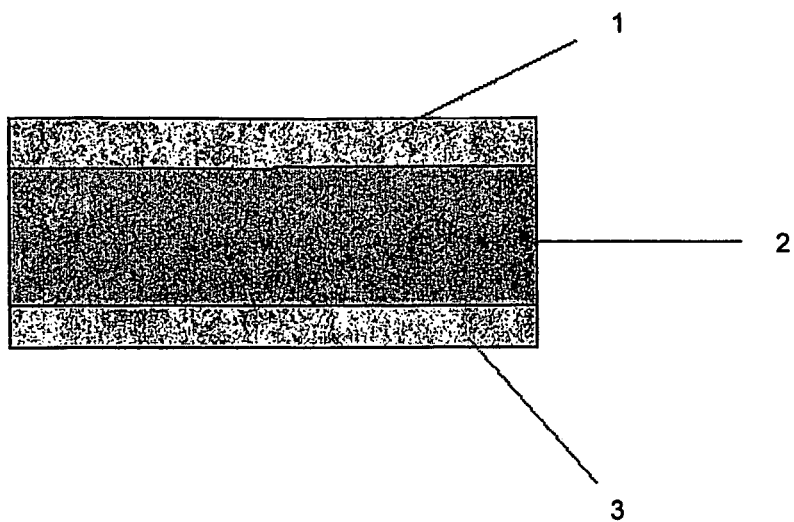

This invention relates to chewing gum in the form of multilayer tablets obtainable by direct compression.

PRIOR ART

Chewing gum is used with increasing frequency as a way of delivering active pharmaceutical or nutraceutical ingredients. The typical manufacturing process requires the base gum to be heated to softening temperature or melted at a temperature of approx. 80° C. in suitable mixers; components such as plasticizer, sweeteners, flavouring agents and possibly other active components of the formulation are added to the molten mass. After mixing, the mass obtained is drawn into strips, cooled and cut to size.

However, although this manufacturing process can be used for thermostable products, it cannot easily be used to prepare systems that carry thermolabile substances such as most drugs and particular active substances such as probiotics.

In order to overcome these limitations, numerous chewing gum manufacturing methods have been proposed, such as those described in U.S. Pat. No. 6,423,336 (Jul. 23, 2002) and WO 02/051258 (Jul. 4, 2002). Chewing gums containing dental hygiene products (patent application US 2002/0071858; Jun. 13, 2002), breath-freshening substances (US 2002/0122843; Sep. 5, 2002) and nutraceutical substances (EP 1254664; Nov. 6, 2002), obtained with a compression process, were recently described. However, in all these patents the description of the manufacturing process is very vague, and nothing is said about the problems that occur during the process of compressing the gum mixtures. One of the major and sometimes insurmountable problems encountered in the process of compressing gum materials is that when the gum bases are compressed, the compacted material adheres strongly, especially to the upper and lower punches of the tablet press, causing obvious problems with the speed and quality of a large-scale production process. This phenomenon is particularly evident in view of the fact that the gum base is adhesive by nature and constitutes the largest proportion of the formulation; moreover, the compression process amplifies this behavior of the material. These problems make the manufacturing process very difficult, and normally require a very low production speed and the use of complex tablet-press cooling systems. One of such process is disclosed for instance in U.S. Pat. No. 4,139,589, disclosing the preparation of multi-layer tablets comprising a core of granular plastic gum base and external layers of non-plastic tablet mass. In order to prevent the adherence of the plastic material to the punches, it is proposed to cool to about −10° C. the plastic mass and/or to use separate and sequential tabletting steps, which considerably limits the process efficiency. Moreover, the surface of the tablet is neither regular nor homogeneous. A further process of coating and/or film-coating is needed to conceal these imperfections, leading to an increase in manufacturing costs.

WO 02/102357 discloses chewing products, wherein a core of gum base containing the active ingredient nicotine is completely included into a buffered coating layer. Said chewing products do not involve any tabletting step and merely requires a coating step of a pre-formed gum core obtained by means of conventional methods. WO 96/03111 discloses pharmaceutical compositions containing medicaments optionally in form of microspheres comprising a core of gum base covered by a film-forming cellulose and polyethylene glycol. Again, this document discloses a process for the manufacture of said compositions including freezing the gum in order to obtain a workable granulate.

DESCRIPTION OF THE INVENTION

It has now been found that the drawbacks of the known technique can be overcome by producing by direct compression tablets containing one or more active pharmaceutical, dietetic or nutritional ingredients comprising at least one inner layer of gum base and at least one outer layer comprising antiadhesion excipients/compression adjuvants.

The term "antiadhesion excipients and compression adjuvants" means any substance or mixture of substances able to coat the inner layer of gum base with one or more layers which promote the process of compression of the system and prevent the punches from adhering to the tablet press.

Only external layers come into contact with the punches during the compression process and the sticking process are solved.

Examples of such antiadhesion excipients include Isomalt, Maltol, Maltodextrin, Maltitol, Mannitol, Xylitol, Lactitol, Lactose, Skim Milk, Eritritol, Oligofructose, Retrograded Starch, polysorbates, polyethyleneoxide, dextrans, Cyclodextrins, Oligosaccarose, fructose, hydrogenated starch hydrosilates.

Particularly preferred are Isomalt, Maltodextrin, Maltitol, Mannitol, Xylitol, Lactitol, Skim Milk, Eritritol, fructose, Oligofructose, dextrans, Oligosaccarose.

Even more preferred are Isomalt, Maltodextrin, Maltitol, Mannitol, Xylitol, Skim Milk, Oligofructose.

The tablets according to the invention preferably consists of a middle layer containing the gum base and an active substance and two outer layers consisting of said antiadhesion excipients and compression adjuvants.

As a consequence of the manufacturing method, the tablets of the invention have a sandwich-like structure, the external layers being not in contact one with the other and respectively coating only the upper and the bottom part of the gum core, leaving the peripheral side thereof uncoated.

Figure 2:
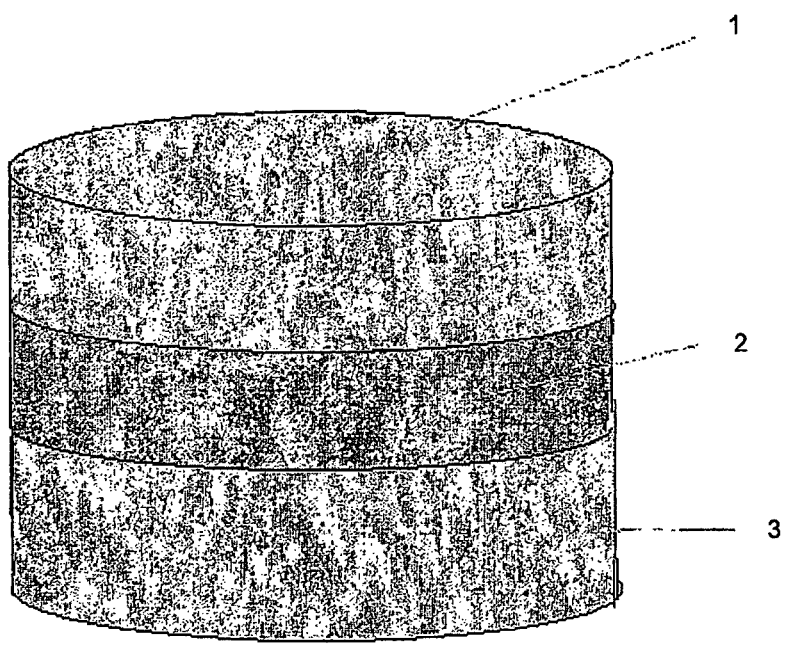

FIGS. 1 and 2 respectively show a side and a perspective view of a three-layer tablet according to the invention wherein the numerals 1 and 3 represent the top and bottom coatings comprising the anti-adhesion excipients whereas the numeral 2 represents the gum core.

Alternatively, the tablets can comprise two, three or more inner layers of gum base, each of which may contain active ingredients which are the same as or different from those present in the other layers, or may be constituted by a formulation with the sole function of separating layers containing incompatible active substances.

The outer layers are the only part of the formulation that comes into contact with the punches during the compression process, so all adherence problems are completely solved, and the difficulties encountered in the process of compressing gum bases only are overcome, particularly it is no longer necessary to subject the gum to freezing to make possible its granulation and subsequent compression in admixture with other ingredients and excipients. The invention also allows continuous, high-speed manufacture using conventional tablet presses. A further advantage of the invention is that the gum base and the active substance carried by it are not heated during the manufacturing process, and are protected by the outer layers during the compression stage.

Thermolabile substances such as drugs, bioactive substances, probiotics, prebiotics, nutritional, food and confectionery substances can be carried by the process according to the invention, either alone or in association with other substances.

The outer layers can also contain an active component which is the same as or different from the one contained in the middle layer.

Examples of drugs contained in one or more layers of the tablets according to the invention include analgesic, antipyretic, anaesthetic, anti-allergic, anti-inflammatory, antifungal and bronchodilator drugs, antibiotics, drugs active on the cardiovascular system, decongestants, disinfectants, expectorants, mucolytics, cough suppressants, anorectics and spasmolytics, together with probiotics, prebiotics, enzymes and the like.

Specific examples of said drugs include acetylsalicylic acid, auranofin, bendazac, benzidamine, diclofenac, diflunisal, etodolac, fenbufen, fenoprofen calcium, flurbiprofen, ibuprofen, indometacin, ketoprofen, ketorolac trometamol, mefenamic acid, naproxen, nimesulide, paracetamol, phenylbutazone, piroxicam, sulindac and suprofen; acetylcysteine, ambroxol hydrochloride, bromexine, carbocysteine, dextromethorphan, guaifenesin, ipecacuanha, levopropoxyphene napsylate, methylcysteine, morclofone, pholcodine, potassium guaicolsulphonate, sobrerol and zipeprol hydrochloride; almitrine dimesylate, amphetamine, carnitine, acetyl carnitine, ciclazindol hydrochloride, dexamphetamine sulphate, dexfenfluramine hydrochloride, amfepramone hydrochloride, doxapram hydrochloride, fenfluramine hydrochloride, benzfetamine hydrochloride, cathinone, dexfenfluramine, diethylpropion hydrochloride, orlistat, sibutramine, sildenafil, apomorphine hydrochloride, tadalafil, vardenafil, methylphenydate hydrochloride, methylamphetamine, pemoline, pentetrazol, fentermine, propylhexedrine; benzalkonium chloride, benzethonium chloride, cetrimide, cetrimonium bromide, cetylpyridinium chloride, chlorhexidine and its salts, chlorocresol, chloroxylenol, chlorophene, cresol, dequalinium chloride, domiphen bromide, hexetidine, hexylresorcinol, ketotifen fumarate, sodium nedocromil, sodium chromoglycate, tiacrilast, alprazolam, amylobarbitone, bromperidol, buspirone hydrochloride, camazepam, chlordiazepoxide, chlormethiazole, chlorpromazine, clobazam, clozapine, diazepam, droperidol, flunitrazepam, fluphenazine decanoate, haloperidol, flurazepam, lorazepam, loxapine, methaqualone, midazolam hydrochloride, nitrazepam, perphenazine, prochlorperazine, promazine, sulpiride, temazepam, zopiclone; trifluoperazine hydrochloride, tetrazepam, tiapride, dopamine hydrochloride, ephedrine hydrochloride, ethylephrine hydrochloride, fenoterol hydrobromide, ibopamine hydrochloride, hydroxyamphetamine hydrobromide, isoprenaline, metaraminol tartrate, methoxamine hydrochloride, naphazoline hydrochloride, noradrenaline hydrochloride, phenylpropanolamine hydrochloride, salbutamol, terbutaline, oxybutinin hydrochloride, propantheline bromide, naloxone hydrochloride, naltrexone hydrochloride, amoxicillin, ampicillin, azithromycin, amphotericin, bacampicillin hydrochloride, cefaclor, cefuroxime axetil, ciprofloxacin, clarithromycin, clindamycin hydrochloride, doxycycline hydrochloride, fusidic acid, minocycline, norfloxacin, rifampicin, fluconazole, itraconazole, nystatin, acyclovir, inosine pranobex, ribavirin, zidovudine, corticosteroids, betamethasone, dexamethasone, hydrocortisone, methylprednisolone, prednisolone, triamcinolone, amitryptiline hydrochloride, clomipramine hydrochloride, desipramine hydrochloride, doxepin hydrochloride, fluoxetine hydrochloride, imipramine hydrochloride, mianserin hydrochloride, nortriptyline hydrochloride, trazodone hydrochloride, tryptophan; vitamins or vitaminic substances in general, essential aminoacids, enzymes, coenzymes, yeasts, probiotics, prebiotics, nutritional and diet supplements herbal extracts, propolis, sodium fluoride, bisacodyl, sodium carbenoxolone, cascara extract, cimetidine, cisapride, dantron, diphenoxylate hydrochloride, docusate calcium, domperidone, famotidine, gefarnate, lactulose, loperamide, lansoprazole, mesalazine, metoclopramide hydrochloride, nizatin, omeprazole, phenolphthalein, ranitidine, senna, sucralfate, sulfasalazine, troxipide, acrivastine, astemizole, brompheniramine maleate, carbinoxamine maleate, chlorpheniramine maleate, cyproheptadine hydrochloride, dimenhydrinate, diphenhydramine, doxylamine succinate, flunarizine hydrochloride, mepyramine, prometazine, terfenadine, tripenellamine, triprolidine, acipimox, bezafibrate, clofibrate, fenofibrate, gemfibrozil, lovastatin, probucol, simvastatin and statins in general, alfentanil hydrochloride, buprenorphine hydrochloride, codeine, dextropropoxyphene, methadone hydrochloride, pentazocine, xanthines such as aminophylline, caffeine, diprophylline, theophylline, disulfiram, ginkgo biloba, papain, pepsin, ubidecarenone and valerian extract.

These components may be contained in a single layer of the chewing gum, either alone or in association, or can be carried in a number of layers. The active component content is between 0.5% and 90% on the weight of the layer which carries said active substance, and preferably between 2 and 60%.

Gum bases with different characteristics and complex compositions, generally with a gum content of between 20% and 98%, and preferably between 30 and 90% by weight, can be used to make chewing gums. Plasticizers selected from the group of polyols such as sorbitol, xylitol, maltitol, isomalt, maltol, mannitol, maltodextrins and cyclodextrins can be added in order to obtain a chewing gum with the optimum organoleptic and chewability characteristics. Said plasticizers are present in a percentage of between 0.5 and 70.0%, and preferably between 1.0 and 50.0% by weight.

Multi-layer chewing gum is made by compressing mixtures of powders and/or granulates; some components or mixtures of components can be previously subjected to conventional treatments such as wet or dry granulation. Multihoppers rotary tabletting machines are preferably used, for instance a three-hopper machine will be used for three layer tablets: in one hopper the gum base composition will be charged whereas the other two will be charged with the anti adhesion excipients. The machine will be suitably programmed for supplying first into the compression die the antiadhesion excipients from a first hopper, followed by the gum base from the second hopper and then the antiadhesion excipients from the third hopper. The excipients in said first and third hoppers may be the same or different.

The process can be carried out at room temperature.

The formulation of each layer may comprise, in addition to the above mentioned antiadhesion excipients, other compression adjuvants commonly used in the pharmaceutical industry, such as lactose, starch, modified starch, microcrystalline cellulose, sorbitol, yclodextrins, saccharose, fructose, dextrose, talc, colloidal silicon dioxide, magnesium stearate, starch paste, methylcellulose, ethylcellulose, polyvinylpyrrolidone, gelatin, pectin and other known adjuvants.

Sweeteners such as saccharose, saccharine, sodium saccharine, aspartame, acesulfame acid and its potassium salt, cyclamic acid, calcium cyclamate, sodium cyclamate, ammonium glycyrrhizinate and other sweeteners commonly used in the food and pharmaceutical industries, such as oligosaccharides, fructose, dextrose, lactose, glucose, maltitol, maltol, maltodextrins, mannitol, sorbitol and xylitol, can also be added. Said sweeteners are present in a percentage by weight of between 0.5 and 50.0%, preferably between 1.0 and 25.0%, and more preferably between 2 and 15%. The formulation can also include flavouring agents in a percentage by weight of between 0.5 and 20.0%, and preferably between 2 and 10.0%.

The invention is illustrated in more detail in the following Examples.

EXAMPLE 1

Preparation of three-layer tablets containing 100 mg of acetylcysteine in the middle layer.
1-a Preparation of Mixture Used for the Outer Layers.
Each outer layer has the following unit composition:

| | |
|---|---|
| Xylitol (Xylisorb) | 100.00 mg |
| Maltodextrin | 100.00 mg |
| Talc (C. Erba) | 5.00 mg |
| Magnesium stearate (C. Erba) | 5.00 mg |
| Colloidal silicon dioxide (Syloid 244 - Grace) | 2.00 mg |
| Mint flavouring (Peppermint) | 5.00 mg |
| Total weight | 217.00 mg |

Xylitol+maltodextrin are mixed for 10 minutes. The remaining components are then added, and mixing continues for a further 20 minutes, to produce a homogeneous mixture.
1-b Preparation of Mixture Constituting the Middle Layer.
The inner layer has the following unit composition:

| | |
|---|---|
| Acetylcysteine (Moehs) | 100.00 mg |
| Gum Base (Flarer - PG Mondo TA) | 500.00 mg |
| Talc (C. Erba) | 10.00 mg |
| Magnesium stearate (C. Erba) | 10.00 mg |
| Colloidal silicon dioxide (Syloid 244 - Grace) | 5.00 mg |
| Mint flavouring (Peppermint) | 5.00 mg |
| Aspartame | 4.00 mg |
| Total weight | 634.00 mg |

The active component and gum base are mixed with flavouring, aspartame and talc, and mixing continues for 10 minutes. The other excipients are then added, and mixing continues for a further 20 minutes, to produce a homogenous, flowable mixture.
1-c Preparation of Three-Layer Chewing Gum by Compression.
The mixture of powders obtained as described in paragraphs 1-a and 1-b, and in accordance with well-known manufacturing processes, is loaded into the three loading hoppers of a rotary tablet press suitable to make three-layer tablets (e.g. Manesty Layer-Press, Liverpool, UK). In particular the mixture described in paragraph 1-a is loaded into the first and third hoppers, and the mixture described in paragraph 1-b is loaded into the second hopper. The tablet press is equipped with flat circular punches with a diameter of 13.0 mm. The machine is regulated to produce three-layer systems consisting of a first layer of 217 mg of the mixture described in paragraph 1-a, a second layer of 634 mg (containing 100 mg of acetylcysteine), and a third and final layer of 217 mg of the mixture described in paragraph 1-a. The amounts contained in the first and third layers are sufficient and necessary to produce an approx. 1.5 mm thickness of said layers. The total weight of the finished system is therefore 1068.00 mg, equivalent to a content of 100 mg of acetylcysteine. Due to the presence of the outer layers, which minimise the contact area between the gum layer and the mechanical parts of the tablet press, the compression process proceeds without difficulty, with a high output, and no adherence to the punches. One of the unsolved problems at the compression stage of a mixture of gum base in direct contact with mechanical parts is strong adherence, which can cause seizure of the punch-die system and can make it impossible to remove the tablets as they are produced, thus making the process impractical on an industrial scale. The tablets obtained with the new process described in the example have a smooth, shiny surface. Their organoleptic characteristics on chewing are a follows: pleasant flavour and rapid gum formation time. On chewing, the gum has an excellent consistency, even when chewed for a long time, and the chewable volume is pleasant. No aftertaste.

REFERENCE EXAMPLE 1b

To test the compressibility characteristics of the layer containing the active component only, tablets with a single layer containing 100 mg of acetylcysteine were prepared.
1-bis-a The Composition Described in Paragraph 1-b of Example 1 is Used.
1-bis-b Preparation of Single-Layer Chewing Gum by Compression.
The mixture of powders obtained as described above, and in accordance with well-known manufacturing processes, is loaded into the loading hopper of a rotary tablet press (e.g. Korsch, Cologne, Germany). The tablet press is equipped with flat circular punches with a diameter of 13.0 mm. The machine is regulated to produce 634 mg tablets (containing 100 mg of acetylcysteine).

The tablets cannot be obtained due to the difficulties encountered in the compression process. The material is compacted, but the tablet produced remains attached to one of the upper or lower punches. The production process must be interrupted immediately because the tablets cannot be removed by the automatic device of the tablet press; they can only be removed manually with a scalpel or other suitable tool, involving considerable effort. The tablet is broken during this operation, and production cannot continue. Another problem that arises is capping of the tablet, because part of the compacted material adheres to the top punch and part to the bottom punch. The result of this comparative test demonstrates the difficulty of manufacturing tablets with a gum base.

EXAMPLE 2

Preparation of three-layer tablets containing 100 mg of carnitine in the middle layer.
2-a Preparation of Mixture Used for the Outer Layers.
Each outer layer has the following unit composition:

| | |
|---|---|
| Maltodextrin | 200.00 mg |
| Talc (C. Erba) | 5.00 mg |
| Magnesium stearate (C. Erba) | 3.00 mg |
| Colloidal silicon dioxide (Syloid 244 - Grace) | 1.00 mg |
| Acesulfame | 3.00 mg |
| Orange flavouring (Givaudan) | 5.00 mg |
| Total weight | 217.00 mg |

The following substances are mixed in a Turbula for 10 minutes: maltodextrin+silicon dioxide; the remaining components are then added, and mixing continues for a further 20 minutes. A homogenous, flowable mixture is obtained.

2-b Preparation of Mixture Constituting the Middle Layer.

The inner layer has the following unit composition:

| | |
|---|---:|
| Carnitine | 100.00 mg |
| Gum Base (Flarer - PG Mondo TA) | 500.00 mg |
| Talc (C. Erba) | 10.00 mg |
| Magnesium stearate (C. Erba) | 10.00 mg |
| Colloidal silicon dioxide (Syloid 244 - Grace) | 5.00 mg |
| Orange flavouring (Givaudan) | 5.00 mg |
| Aspartame | 4.00 mg |
| Total weight | 634.00 mg |

Flavouring, aspartame and talc are added to the gum, and mixing continues for 10 minutes. The other excipients and the active component are then added and mixing continues for a further 20 minutes, to produce a homogeneous, flowable mixture.

2-c Preparation of Three-Layer Chewing Gums by Compression.

The mixture of powders obtained as described in paragraphs 2-a and 2-b, and in accordance with well-known manufacturing processes, is loaded into the three loading hoppers of a rotary tablet press suitable to make three-layer tablets (e.g. Manesty Layer-Press, Liverpool, UK). In particular the mixture described in paragraph 2-a is loaded into the first and third hoppers, and the mixture described in paragraph 2-b is loaded into the second hopper. The tablet press is equipped with flat circular punches with a diameter of 13.0 mm. The machine is regulated to produce three-layer systems consisting of a first layer of 217 mg of the mixture described in paragraph 2-a, a second layer of 634 mg (equivalent to 100 mg of carnitine), and a third and final layer of 217 mg of the mixture described in paragraph 2-a. The amounts contained in the first and third layers are sufficient and necessary to produce an approx. 1.5 mm thickness of said layers.

The total weight of the finished system is therefore 1068 mg, equivalent to a content of 100 mg of carnitine. The compression process proceeds without difficulty, at a high production speed, with no adherence to the punches. This test confirms that the innovative dosage form and the process allow efficient industrial production.

The tablets (chewing gum) obtained have a smooth, shiny surface. Their organoleptic characteristics on chewing are as follows: acceptable flavour, rapid gum formation, excellent consistency, no after-taste.

EXAMPLE 3

Preparation of three-layer tablets, containing 10 mg of caffeine in the middle layer.

3-a Preparation of Mixture Used for the Outer Layers.

Each outer layer has the unit composition described in example 1a.

3-b Preparation of Mixture Constituting the Middle Layer.

The inner layer has the following unit composition:

| | |
|---|---:|
| Caffeine (C. Erba) | 10.00 mg |
| Gum Base (Flarer - PG Mondo TA) | 500.00 mg |
| Talc (C. Erba) | 10.00 mg |
| Magnesium stearate (C. Erba) | 10.00 mg |
| Colloidal silicon dioxide (Syloid 244 - Grace) | 5.00 mg |
| Mint flavouring (Peppermint) | 10.00 mg |
| Aspartame | 5.00 mg |
| Total weight | 550.00 mg |

Flavouring, aspartame and talc are added to the gum base mixed with caffeine, and mixing continues for 10 minutes. The other excipients are then added and mixing continues for a further 20 minutes, to produce a homogeneous, flowable mixture.

3-c Preparation of Three-Layer Chewing Gums by Compression.

The mixture of powders obtained as described in paragraphs 3-a and 3-b, and in accordance with well-known manufacturing processes, is loaded into the three loading hoppers of a rotary tablet press suitable to make three-layer tablets (e.g. Manesty Layer-Press, Liverpool, UK). The total weight of the finished system is therefore 984.00 mg, equivalent to a content of 10 mg of caffeine.

The compression process proceeds without difficulty, at a high production speed, with no adherence to the punches. The tablets obtained have a smooth, shiny surface. Their organoleptic characteristics on chewing are as follows: acceptable flavour, very fast gum formation time, efficacious chewable volume with excellent consistency, and a slightly bitter aftertaste.

3-d Evaluation of Release of Active Component In Vivo.

To establish the release of active component from the chewing gum, the tablets were tested by a panel of 3 volunteers. For each test, the volunteer was asked to chew one piece of gum for a set time. After that time the gum was ground, and the active component content analysed. The in vivo tests were conducted with the following chewing times: 5, 10, 15, 20, 30 and 40 minutes. The gum residue was weighed, frozen and finely ground. An exactly weighed amount of this powder was then subjected to the dissolution test according to the American Pharmacopoeia, using 1000 mL of water at 37° as dissolving fluid, and a paddle at 100 rpm. The test was performed by the spectrophotometry method, operating at 273 nm. The amount of active component released in vivo was determined by subtracting the amount of caffeine in the residue from the amount present in the pharmaceutical form.

Table I shows the percentages of caffeine released after various chewing times.

TABLE I

| Chewing time | Volunteer 1 | Volunteer 2 | Volunteer 3 | Caffeine released in vivo (average) | SD |
|---|---|---|---|---|---|
| 5 minutes | 71.52 | 77.02 | 75.07 | 74.54 | 2.79 |
| 10 minutes | 86.03 | 83.66 | 84.94 | 84.88 | 1.19 |
| 15 minutes | 90.18 | 90.97 | 91.07 | 90.74 | 0.49 |
| 20 minutes | 89.45 | 91.58 | 89.61 | 90.21 | 1.19 |
| 30 minutes | 93.92 | 92.25 | 92.49 | 92.89 | 0.90 |
| 40 minutes | 92.79 | 93.34 | 92.34 | 92.82 | 0.50 |

As will be seen, approx. 75% of the dose of the drug is released after 5 minute chewing, and over 90% of the active component is fully released after 15 minutes. Chewing for a further 25 minutes does not lead to any significant variation in the amount of active component released by the gum. The in vivo results confirm that the active component contained in the pharmaceutical form is readily available for absorption. The results of the various tests are highly reproducible, as demonstrated by the low standard deviation, which confirms that the release of the drug from the medicated chewing gum is independent of the efficacy of chewing by the volunteers, and consequently guarantees wide applicability of this innovative pharmaceutical form.

EXAMPLE 4

Preparation of a set of three-layer tablets (chewing gum) containing 3 mg of benzydamine hydrochloride in the middle layer.

4-a Preparation of Mixture Used for the Outer Layers.

Each outer layer has the following percentage composition:

| | |
|---|---|
| Isomalt | 85.10% |
| Fructose (C. Erba) | 7.66% |
| Talc (C. Erba) | 2.13% |
| Colloidal silicon dioxide (Syloid 244 - Grace) | 0.85% |
| Magnesium stearate (C. Erba) | 2.13% |
| Mint flavouring (Givaudan Roure) | 2.13% |
| Total weight | 100.00% |

All the other components were added to the mixture of isomalt and colloidal silicon dioxide, and mixing continued for 20 minutes, to produce a homogeneous, flowable mixture subsequently subjected to the compression stage described below.

4-b Preparation of Mixture Constituting the Middle Layer.

The middle layer has the following unit composition:

| | |
|---|---|
| Benzydamine hydrochloride | 3.00 mg |
| Gum Base (Flarer - PG Mondo TA) | 450.00 mg |
| Talc (C. Erba) | 5.00 mg |
| Colloidal silicon dioxide (Syloid 244 - Grace) | 2.00 mg |
| Magnesium stearate (C. Erba) | 5.00 mg |
| Mint flavouring (Givaudan Roure) | 5.00 mg |
| Lemon flavouring (Givaudan Roure) | 10.00 mg |
| Aspartame | 10.00 mg |
| Total weight | 490.00 mg |

All the components, previously sieved through a 25 mesh grid (equal to 710 microns), are poured into a suitable mixer, and after 20 minute stirring a homogeneous, flowable mixture is obtained which is subjected to the compression stage described in paragraph 4-c.

4-c Preparation of Three-Layer Tablets by Compression.

The mixtures of powders obtained as described in paragraphs 4-a and 4-b, and in accordance with well-known manufacturing processes, are loaded into the three loading hoppers of a rotary tablet press suitable to make three-layer tablets (e.g. Manesty Layer-Press, Liverpool, UK). The total weight of the finished system is therefore 990 mg, equivalent to a content of 3 mg of benzydamine hydrochloride. The compression process proceeds without difficulty, at a high production speed, with no adherence to the punches. The tablets obtained have a smooth, shiny surface. Their organoleptic characteristics on chewing are as follows: fast gum formation time, pleasant chewable volume with an excellent consistency, a slightly astringent flavour and no after-taste.

EXAMPLE 5

Preparation of four-layer tablets, containing 50 mg of levodopa in layer 2 and 12.5 mg of carbidopa in layer 3.

5-a Preparation of Mixture for the First and Fourth Layers.

Each layer has the following unit composition:

| | |
|---|---|
| Fructo-oligosaccharide | 150.00 mg |
| Fructose (C. Erba) | 10.00 mg |
| Talc (C. Erba) | 5.00 mg |
| Colloidal silicon dioxide (Syloid 244 - Grace) | 1.00 mg |
| Magnesium stearate (C. Erba) | 2.00 mg |
| Chocolate flavouring (Givaudan Roure) | 10.00 mg |
| Hazelnut flavouring (Givaudan Roure) | 5.00 mg |
| Total weight | 183.00 mg |

All pre-sieved components are placed in a suitable container and mixed for 20 minutes. The homogeneous, flowable mixture is then subjected to the compression stage described below.

5-b Preparation of Mixture Constituting the Middle Layer.

The middle layer has the following unit composition:

| | |
|---|---|
| Levodopa | 50.00 mg |
| Gum Base (Flarer - Unique 90%) | 250.00 mg |
| Talc (C. Erba) | 2.00 mg |
| Colloidal silicon dioxide (Syloid 244 - Grace) | 0.50 mg |
| Magnesium stearate (C. Erba) | 1.00 mg |
| Chocolate flavouring (Givaudan Roure) | 5.00 mg |
| Total weight | 308.50 mg |

All the components, previously sifted through a 25 mesh grid (equal to 710 microns), are poured into a suitable mixer, and after 20 minute stirring a homogeneous, flowable mixture is obtained which is subjected to the compression stage described in paragraph 5-d.

5-c Preparation of Mixture Constituting the Middle Layer.

The middle layer has the following unit composition:

| | |
|---|---|
| Carbidopa | 12.50 mg |
| Gum Base (Flarer - Unique 90%) | 250.00 mg |
| Talc (C. Erba) | 2.00 mg |
| Colloidal silicon dioxide (Syloid 244 - Grace) | 0.50 mg |
| Magnesium stearate (C. Erba) | 1.00 mg |
| Chocolate flavouring (Givaudan Roure) | 5.00 mg |
| Total weight | 271.00 mg |

All the components, previously sieved through a 25 mesh grid (equal to 710 microns), are poured into a suitable mixer, and after 20 minute stirring a homogeneous, flowable mixture is obtained which is subjected to the compression stage described in paragraph 5-d.

5-d Preparation of Four-Layer Tablets by Compression.

The mixture of powders obtained as described in paragraphs 5-a, 5-b and 5-c, and in accordance with well-known manufacturing processes, is loaded into the loading hoppers of a rotary tablet press suitable to make multi-layer tablets (e.g. Korsch). In particular, the mixture described in paragraph 5-a is loaded into the first and fourth hoppers, the mixture described in paragraph 5-b is loaded into the second hopper, and the mixture described in paragraph 5-c is loaded into the third hopper. The tablet press is equipped with convex circular punches with a diameter of 12.0 mm and regulated to produce four-layer systems consisting of a first layer of 183 mg of mixture 5-a, a second layer of 308.5 mg (equal to 50 mg of levodopa), a third layer of 271 mg (equal to 12.5 mg of carbidopa), and a fourth layer of 183 mg of the mixture described in paragraph 5-a. The amounts contained in the first and fourth layers are sufficient and necessary to produce an approx. 1.5 mm thickness of said layers. The total weight of the finished system is therefore 945 mg, equivalent to a content of 50 mg of levodopa and 12.5 mg of carbidopa. The compression process proceeds without difficulty, at a high production speed, with no adherence to the punches. The tablets obtained have a smooth, shiny surface. On chewing, the tablet presents a fast gum formation time, a pleasant chewable volume with an excellent consistency, a slightly astringent flavour and no after-taste.

The tablets were then subjected to the dissolution test according to the American Pharmacopoeia method, using 1000 mL of water at 37° as dissolving fluid and a paddle at 100 rpm. The test was performed by the spectrophotometry method, operating at 280 nm.

Table II shows the percentages of levodopa and carbidopa released by the tablets.

TABLE II

| Time (min) | levodopa | SD of levodopa | carbidopa | SD of carbidopa |
|---|---|---|---|---|
| 0 | 0.00 | 0.00 | 0.00 | 0.00 |
| 5 | 63.52 | 8.08 | 78.23 | 2.54 |
| 15 | 90.00 | 4.74 | 92.63 | 0.96 |
| 20 | 92.47 | 4.46 | 94.97 | 0.74 |
| 25 | 94.04 | 4.08 | 96.55 | 0.82 |
| 30 | 94.90 | 4.01 | 98.18 | 0.71 |
| 35 | 95.66 | 3.92 | 98.77 | 0.77 |
| 40 | 96.28 | 3.84 | 100.00 | 0.00 |

The invention claimed is:

1. Chewing gum tablets containing one or more active pharmaceutical, dietetic or nutritional ingredients, said tablets comprising at least one inner core layer of gum base and a plurality of outer layers not in contact one with the other and respectively coating only the upper and bottom part of the gum core, leaving the peripheral side of the core uncoated, said outer layers consisting of compressed mixtures of powders, wherein said at least one inner layer of gum base comprises a gum component that is between 20 and 98% of the base; and said outer layers comprise antiadhesion excipients and compression adjuvants selected from isomalt, maltol, maltodextrin, maltitol, mannitol, xylitol, lactitol, lactose, skim milk, eritritol, oligofructose, retrograded starch, polysorbates, polyethyleneoxide, dextrans, cyclodextrins, oligosaccharose, fructose, and hydrogenated starch hydrosilates.

2. Tablets as claimed in claim 1, comprising two, three or more inner layers of gum base, wherein each inner layer contains active ingredients which are the same as or different from those present in the other layers.

3. Tablets as claimed in claim 1, wherein the one or more active ingredients is present in one or more of the plurality of outer layers.

4. Tablets as claimed in claim 1, obtainable by direct compression of the mixtures of powders or granulates of each layer.

5. Tablets as claimed in claim 2, wherein the active ingredients are selected from analgesic, antipyretic, anaesthetic, anti-allergic, anti-inflammatory, antifungal and bronchodilator drugs, antibiotics, drugs active on the cardiovascular system, decongestants, disinfectants, expectorants, mucolytics, cough suppressants, anorectics, spasmolytics, probiotics, probiotics, and enzymes.

6. Tablets as claimed in claim 1, wherein the layers of gum base contain a plasticizer selected from sorbitol, xylitol, maltitol, isomalt, maltol, mannitol, maltodextrins and cyclodextrins.

7. Tablets as claimed in claim 6, wherein said plasticizer is present in the percentage of between 0.5 and 70.0% by weight.

8. A process for the preparation of the tablets of claim 1, comprising
subjecting to direct tabletting in a multi-hopper machine a gum base composition containing anti adhesion excipients,
supplying first into a compression die a first portion of the antiadhesion excipients from a first hopper, followed by a gum base from a different hopper, and then a second portion of antiadhesion excipients from a third hopper and subjecting to compression the resulting layers.

9. Tablets obtainable by the process of claim 8.

10. Tablets as claimed in claim 1 wherein the active component content is between 2% and 60% on the weight of the layer in which said active component is carried.

11. Tablets as claimed in claim 2, wherein the active component content is between 2 and 60% on the weight of the layer in which said active component is carried.

* * * * *